United States Patent [19]

Kitagawa et al.

[11] Patent Number: 4,935,527

[45] Date of Patent: Jun. 19, 1990

[54] PRODUCTION OF AZIRIDINE-2-CARBOXYLIC ACID SALTS

[75] Inventors: Sadao Kitagawa; Takashi Yokoi; Mitsumasa Kaitoh, all of Ami, Japan

[73] Assignee: Research Association for Utilization of Light Oil, Tokyo, Japan

[21] Appl. No.: 289,440

[22] Filed: Dec. 23, 1988

Related U.S. Application Data

[63] Continuation of Ser. No. 858,549, Feb. 12, 1986, abandoned.

[30] Foreign Application Priority Data

Feb. 13, 1985 [JP] Japan ................................. 60-25775
Jul. 19, 1985 [JP] Japan ................................. 60-159498

[51] Int. Cl.$^5$ ........................................... C07D 203/00
[52] U.S. Cl. ................................................. 548/966
[58] Field of Search ....................................... 548/966

[56] References Cited

U.S. PATENT DOCUMENTS 4,393,000  7/1983  Mita et al. ........................... 548/966

FOREIGN PATENT DOCUMENTS 30475   1/1981  European Pat. Off. .
30870   1/1981  European Pat. Off. .
171787  2/1986  European Pat. Off. .
207373  1/1960  Fed. Rep. of Germany ...... 548/966
1126879 4/1962  Fed. Rep. of Germany .
1366224 9/1974  United Kingdom .

OTHER PUBLICATIONS

Auclair, et al., Chem. Abstracts, vol. 82 (1975), entry 77485n.
Devos, et al., Chem. Abstracts, vol. 94 (1981), entry 67590b.
Schoenrock, et al., Chem. Abstracts, vol. 83 (1975), entry 62354r.
European Search Report.

*Primary Examiner*—Mukund J. Shah
*Assistant Examiner*—C. L. Cseh
*Attorney, Agent, or Firm*—Oblon, Spivak, McClelland, Maier & Neustadt

[57] ABSTRACT

Alkaline earth metal salts of aziridine-2-carboxylic acid, typically Ca salt, are produced by a reaction of a 2,3-dihalopropionic acid derivative or an α-haloacrylic acid derivative with an aqueous ammonia in the presence of an alkaline earth metal hydroxide, typically Ca(OH)$_2$.

Salts of aziridine-2-carboxylic acid are recovered from such a reaction product as referred to above by a liquid chromatographic technique in which a weak or weakened cation exchanger is utilized.

15 Claims, 1 Drawing Sheet

PRODUCTION OF AZIRIDINE-2-CARBOXYLIC ACID SALTS

This application is a continuation of application Ser. No. 06/858,549, filed on Feb. 12, 1986, now abandoned.

BACKGROUND OF THE INVENTION

1. Field of the Art

The present invention relates to the production of aziridine-2-carboxylic acid salts, more particularly to (1) the synthesis of aziridine-2-carboxylic acid salts, particularly calcium or barium salt, and (2) the recovery of the aziridine-2-carboxylic acid salts according particularly to a liquid chromatography.

The aziridine-2-carboxylic acid salts themselves and their derivatives have physiological activities such as antineoplastic activities, and they are useful as intermediates or starting materials for α-amino acids such as serine, medicines, pesticides and functional resins.

2. Prior Art and Problems

For the synthesis of metal salts of aziridine-2-carboxylic acid, the following processes have been known:

(1) a process wherein a 2,3-dibromopropionic acid ester is reacted with liquid ammonia, and the resulting aziridine-2-carboxylic acid ester is reacted with an alkali metal or alkaline earth metal hydroxide in water to form a salt of aziridine-2-carboxylic acid [E. Kyburz et al., Helv. Chim. Acta 49 (1), 359 (1966) and K. D. Gundermann et al., Chem. Ber. 93, 1632 (1960)];

(2) a process wherein an α-halo-β-aminopropionitrile or its mineral acid salt is reacted with an alkali metal or alkaline earth metal hydroxide in water or a hydrous organic solvent to form an aziridine-2-carboxylic acid salt (see the specification of Japanese Patent Laid-Open No. 83470/1981); and (3) a process wherein a 2,3-dihalopropionitrile or α-haloacrylonitrile is reacted with ammonia in water or a hydrous organic solvent to form an α-halo-β-aminopropionitrile which is then reacted with an alkali metal or alkaline earth metal hydroxide without isolation of the α-halo-β-aminopropionitrile to form a salt of aziridine-2-carboxylic acid (see the specifications of Japanese Patent Laid-Open Nos. 90055/1981 and 100759/1981).

Though the above-mentioned processes are valuable, they still have some problems. That is, the process (1) is industrially disadvantageous since the yield of the aziridine-2-carboxylic ester is low, and the recovery of this compound in a step of purification by distillation is also low because the aziridine-2-carboxylic acid ester per se is unstable. The process (2) cannot be recommended from an industrial viewpoint since the α-halo-β-aminopropionitrile is unstable. For handling this compound stably, it should be converted into a mineral acid salt thereof by quite complicated steps. Although the drawbacks of the process (2) are overcome to some extent by the process (3), the formed, unstable α-halo-β-aminopropionitrile must be reacted immediately with an alkali metal or alkaline earth metal hydroxide. The requirements of this treatment are insufficient from the industrial viewpoint.

Thus, it cannot be considered that the processes for the production of the aziridine-2-carboxylic acid salts on an industrial scale have been completely developed.

On the other hand, for the recovery of the aziridine-2-carboxylic acid salts, the following processes wherein an aziridine-2-carboxylic acid ester obtained by reacting a 2,3-dibromopropionic acid ester with ammonia is used have been known:

(1) a process wherein: an aqueous lithium hydroxide solution is added to a solution of ethyl aziridine-2-carboxylate in ethanol to carry out the reaction in a cold place; the reaction product is dried under reduced pressure to obtain a syrup; then benzene is added to the syrup; the mixture is subjected to an azeotropic distillation to remove residual water; anhydrous ethanol is added thereto; and lithium aziridine-2-carboxylate thus precipitated is recovered [the above-mentioned Chem. Ber. 93, 1632 (1960)].

(2) a process wherein: a solution of metallic sodium in a mixture of ethanol and ether is added to a solution of isopropyl aziridine-2-carboxylate; the mixture is stirred together with a small amount of water to form sodium aziridine-2-carboxylate precipitate; and this precipitate is recovered [the above-mentioned Helv. Chim. Acta., 49, 359 (1966)].

These processes have a problem in that the yield of the starting aziridine-2-carboxylic acid ester itself is poor and that the recovery of the product ester in the step of the purification by distillation or the like is also poor since the aziridine-2-carboxylic acid ester per se is unstable. Further, for the recovery of solid aziridine-2-carboxylic acid salts from its solution, an industrially satisfactory process has not yet been developed. Since complicated treatments such as concentration to dryness under reduced pressure, azeotropic distillation, addition of a precipitating agent such as ethanol or ether and recovery by filtration are necessitated, the recovery of the aziridine-2-carboxylic acid salt is poor, and repurification is necessary for obtaining a highly pure product because such a compound having a high hygroscopicity as sodium aziridine-2-carboxylate frequently contains impurities.

Although several industrially advantageous processes for the production of aziridine-2-carboxylic acid salts have been proposed (see, for example, the specifications of the above-mentioned Japanese Patent Laid-Open Nos. 90055/1981 and 100759/1981), the reaction liquid obtained by these processes contains a large amount of an inorganic salt in addition to the aziridine-2-carboxylic acid salt. The presence of such an impurity is undesirable when the aziridine-2-carboxylic acid salt thus obtained is used directly as a starting material for medicines, pesticides or serine for which they have been used mainly heretofore. Particularly, the presence of a halogen ion reduces the yield of the intended product seriously when, for example, serine is to be produced from the aziridine-2-carboxylic acid salt. However, the highly pure aziridine-2-carboxylic acid salt cannot be obtained from an aqueous solution thereof containing the inorganic salt by the known recovering processes.

In our experiments wherein ethanol used as a precipitating agent was added to an aqueous solution containing an aziridine-2-carboxylic acid salt, an inorganic salt and other impurities, the formed precipitate contained the inorganic salt in addition to the aziridine-2-carboxylic acid salt, and, therefore, this process could not be employed as an effective process for recovering highly pure aziridine-2-carboxylic acid salt (see Comparative Example B2 given below).

Therefore, for obtaining aziridine-2-carboxylic acid salts of high purity, the use of the following process wherein an inorganic salt is substantially not by-produced in the production of the aziridine-2-carboxylic acid has been unavoidable.

(3) a process wherein triethanolamine is added to a solution of ethyl α-chloro-β-aminopropionate hydrochloride in ethanol to precipitate triethanolamine hydrochloride; this precipitate is filtered out; an aqueous lithium hydroxide solution is added to the filtrate to carry out the reaction in a cold, dark place for 24 h; the reaction mixture is concentrated to dryness under reduced pressure to obtain a syrup; benzene is added to the syrup; water remaining therein is removed by an azeotropic distillation; ethanol and ether are added thereto; and the thus formed lithium aziridine-2-carboxylate is recovered (see "process for the synthesis of the standard" given in the specification of the above-mentioned Japanese Patent Laid-OPen No. 83470/1981).

Thus, a practicable technique has not yet been developed, although the development of a process for recovering the quite useful aziridine-2-carboxylic acid salts by the separation from inorganic salts and other impurities efficiently in an industrially advantageous manner has been eagerly sought.

SUMMARY OF THE INVENTION

After intensive investigations made for the purpose of developing a process for producing aziridine-2-carboxylic acid salts in a high yield from a 2,3-dihalopropionic acid derivative or α-haloacrylic acid derivative in one step, we have developed the present invention.

In one aspect thereof, the process of the present invention for the production of alkaline earth metal salts of aziridine-2-carboxylic acid is characterized in that a 2,3-dihalopropionic acid derivative of the following general formula (AI) or an α-haloacrylic acid derivative of the general formula (AII) is reacted with ammonia in the presence of an alkaline earth metal hydroxide which is $Ca(OH)_2$ or $Ba(OH)_2$ in an aqueous medium:

(AI)

(AII)

wherein: X represents a halogen atom selected from the group consisting of fluorine, chlorine, bromine and iodine, and Y represents $-CO_2R^1$, $-CONR^2_2$ or $-CN$ group, $R^1$ being a hydrocarbon residue having 1 to 10 carbon atoms and $R^2$ being a hydrogen atom or a hydrocarbon residue having 1 to 10 carbon atoms.

In another aspect thereof, the present invention has been arrived at and developed after intensive investigations made for the purpose of developing a process for efficiently recovering the aziridine-2-carboxylic acid salts by isolating the same from inorganic salts and other impurities under these circumstances.

The process of the present invention for recovering the aziridine-2-carboxylic acid salts is characterized by comprising the steps of feeding an aqueous solution of an aziridine-2-carboxylic acid salt containing an inorganic salt as an impurity into a front end of a packed bed containing a cation exchanger selected from the group consisting of a strongly acidic cation exchanger of a metal salt form, weakly acidic cation exchanger of a metal salt form and a weakly acidic cation exchanger of H-form, then feeding water therein and taking a fraction of the aziridine-2-carboxylic acid salt eluted at a rear end of the packed bed.

In the first aspect of the present invention, the reaction operation is easy and the reaction device can be simplified economically advantageously since the intended calcium or barium aziridine-2-carboxylate can be produced in a high yield from a starting 2,3-dihalopropionic acid derivative or α-haloacrylic acid derivative in one step.

Further, the process of the present invention is economically excellent, since calcium hydroxide used as a typical alkali is the least expensive.

It is to be noted that the alkalis used in the present invention are limited to alkaline earth metal hydroxides which are $Ca(OH)_2$ and $Ba(OH)_2$. For example, when calcium hydroxide used as the alkaline earth metal hydroxide is replaced with sodium hydroxide, the yield of formed sodium aziridine-2-carboxylate is surprisingly very poor (see Comparative Examples A1 and A2).

The reasons why such a difference in the yield is caused depending on the variety of the alkali and the mechanism of the formation of calcium or barium aziridine-2-carboxylate from the 2,3-dihalopropionic acid derivative or α-haloacrylic acid derivative in one step have not yet been elucidated.

Such a process for producing the aziridine-2-carboxylic acid salts from the 2,3-dihalopropionic acid derivatives or α-haloacrylic acid derivatives in only one reaction step has not yet been proposed. Further, it could not be inferred from known techniques that the aziridine-2-carboxylic acid salts can be obtained in a high yield only when the alkalis used in the reaction are limited to alkaline earth metal hydroxides. Thus, the process of the present invention has been completed on the basis of the surprising findings.

In the other aspect thereof, the present invention provides a process for recovering a highly pure aziridine-2-carboxylic acid salt in the form of its aqueous solution from an aqueous solution of the aziridine-2-carboxylic acid salt containing an inorganic salt by separating not only the inorganic salt but also other impurities such as by-products formed by side reactions from the aqueous solution. The process of the present invention has industrial advantages in that the intended product can be recovered by a simple treatment of introducing the liquid sample and water into a packed column containing a cation exchanger, in that the cation exchanger can be used repeatedly substantially without necessitating regeneration after the introduction of the sample and water, and in that high cost for a regenerating agent is unnecessary. This is economically quite advantageous.

The aqueous solution of the aziridine-2-carboxylic acid salt recovered by the process of the present invention has a high purity, and, therefore, it can be used for a desired purpose as it is or after concentration or, alternatively, the solid aziridine-2-carboxylic acid salt can be obtained by concentration and/or addition of a precipitating agent.

DETAILED DESCRIPTION OF THE PREFERRED EMBODIMENT

SYNTHESIS OF THE SALTS

Figure 1:
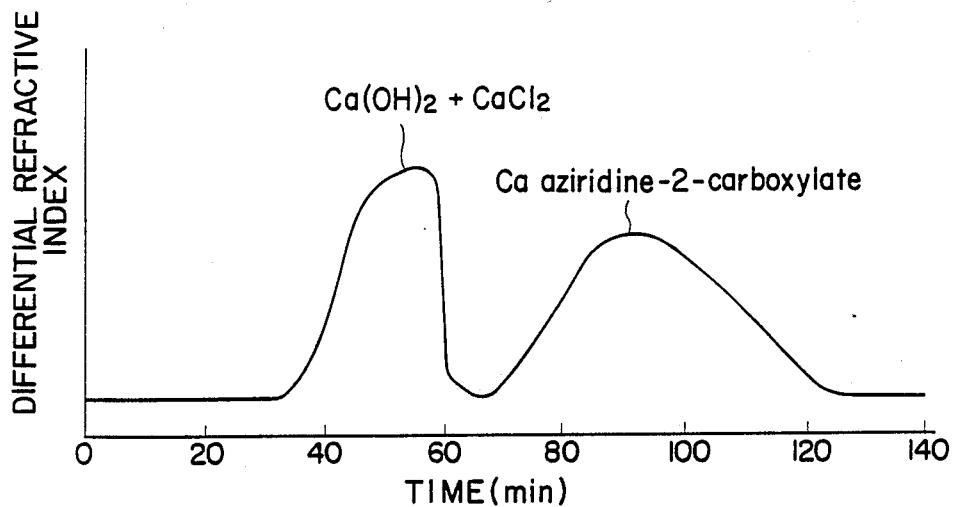
FIG. 1 is a graph showing an elution curve obtained when an aqueous solution containing 8.81% of calcium aziridine-2-carboxylate, 9.60% of calcium chloride, 0.10% of calcium hydroxide and side reaction products was charged in a column containing a strongly acidic cation exchange resin of $Ca^{2+}$ form and then distilled water was introduced therein at 25° C.

In the first aspect of the present invention, the process for the production of the aziridine-2-carboxylic acid salts comprises reacting a specified $C_3$-carboxylic acid derivative with an alkali in an aqueous medium.

2,3-Dihalopropionic acid derivatives and α-haloacrylic acid derivatives

The 2,3-dihalopropionic acid derivatives and α-haloacrylic acid derivatives used in the present invention are represented by the above formulae (AI) and (AII), respectively. In the formulae, X is preferably chlorine or bromine. From the economical viewpoint, chlorine is particularly preferred. $R^1$ is a hydrocarbon residue having 1 to 10 carbon atoms, preferably 1 to 5 carbon atoms and more preferably 1 to 3 carbon atoms, and $R^2$ is a hydrogen atom or a hydrocarbon residue having 1 to 10 carbon atoms, preferably a hydrogen atom or a hydrocarbon residue having 1 to 3 carbon atoms and more preferably a hydrogen atom.

Examples of the 2,3-dihalopropionic acid derivatives and α-haloacrylic acid derivatives include: methyl 2,3-dichloropropionate; ethyl 2,3-dichloropropionate; n-propyl 2,3-dichloropropionate; i-propyl 2,3-dichloropropionate; butyl 2,3-dichloropropionate; amyl 2,3-dichloropropionate; octyl 2,3-dichloropropionate; decyl 2,3-dichloropropionate; phenyl 2,3-dichloropropionate; benzyl 2,3-dichloropropionate; naphthyl 2,3-dichloropropionate; 2,3-dichloropropionic acid amide; 2,3-dichloropropionic acid N-methylamide; 2,3-dichloropropionic acid N,N-dimethylamide; 2,3-dichloropropionic acid N,N-diethylamide; 2,3-dichloropropionic acid N-propylamide; 2,3-dichloropropionic acid N,N-dipropylamide; 2,3-dichloropropionic acid N-amylamide; 2,3-dichloropropionic acid N-octylamide; 2,3-dichloropropionic acid N-decylamide; 2,3-dichloropropionitrile; methyl α-chloroacrylate; ethyl α-chloroacrylate; propyl α-chloroacrylate; butyl α-chloroacrylate; amyl α-chloroacrylate; hexyl α-chloroacrylate; octyl α-chloroacrylate; cyclohexyl α-chloroacrylate; decyl α-chloroacrylate; phenyl α-chloroacrylate; naphthyl α-chloroacrylate; α-chloroacrylamide; α-chloro-N-methylacrylamide; α-chloro-N,N-dimethylacrylamide; α-chloro-N-ethylacrylamide; α-chloro-N,N-diethylacrylamide; α-chloro-N-propylacrylamide; α-chloro-N,N-dipropylacrylamide; α-chloro-N-butylacrylamide; α-chloro-N-hexylacrylamide; α-chloro-N-decylacrylamide; α-chloro-N-phenylacrylamide; α-chloro-N-naphthylacrylamide; α-chloroacrylotririle and corresponding compounds having fluorine, bromide or iodine in place of chlorine.

Among these compounds, preferred examples include methyl 2,3-dichloropropionate; ethyl 2,3-dichloropropionate; n-propyl 2,3-dichloropropionate; i-propyl 2,3-dichloropropionate; butyl 2,3-dichloropropionate; amyl 2,3-dichloropropionate; 2,3-dichloropropionic acid amide; 2,3-dichloropropionic acid N-methylamide; 2,3-dichloropropionic acid N,N-dimethylamide; 2,3-dichloropropionic acid N-ethylamide; 2,3-dichloropropionic acid N,N-diethylamide, 2,3-dichloropropionic acid N-propylamide; 2,3-dichloropropionic acid N,N-dipropylamide; 2,3-dichloropropionitrile; methyl α-chloroacrylate; ethyl α-chloroacrylate; propyl α-chloroacrylate; butyl α-chloroacrylate; amyl α-chloroacrylate; α-chloroacrylamide; α-chloro-N-methylacrylamide; α-chloro-N-ethylacrylamide; α-chloro-N,N-dimethylacrylamide; α-chloro-N-ethylacrylamide; α-chloro-N,N-diethylacrylamide; α-chloro-N-propylacrylamide; α-chloro-N,N-dipropylacrylamide; α-chloroacrylonitrile and corresponding compounds containing bromine in place of chlorine.

Particularly preferred examples of these compounds include methyl 2,3-dichloropropionate; ethyl 2,3-dichloropropionate; n-propyl 2,3-dichloropropionate; 2,3-dichloropropionic acid amide; 2,3-dichloropropionitrile; methyl α-chloroacrylate; ethyl α-chloroacrylate; propyl α-chloroacrylate; α-chloroacrylamide; and α-chloroacrylonitrile.

These compounds have been well known. Those prepared by a suitable process may be used as the starting materials in the present invention.

Aqueous medium/alkaline earth metal hydroxides

The reaction media used in the present invention are aqueous media, particularly, water and mixtures of water and an organic solvent.

The organic solvents which may be used together with water include alcohols such as methanol, ethanol, n-propanol, i-propanol, n-butanol, i-butanol ethylene glycol and cellosolves; ethers such as dioxane, tetrahydrofuran, diethyl ether and diisopropyl ether; acetone; N,N-dimethylformamide; dimethyl sulfoxide; and hydrocarbons such as hexane, toluene and xylene. Among them, methanol, ethanol and i-propanol are preferred. The amount of water contained in the organic solvent is at least 2 mol per mol of the 2,3-dihalopropionic acid derivative or α-haloacrylic acid derivative.

Among these solvents, water alone is particularly preferred.

The amount of the aqueous medium used is such that the concentration of the 2,3-dihalopropionic acid derivative or α-haloacrylic acid derivative (hereinafter referred to as substrate) will be in the range of about 0.1 to 50 wt.%, preferably 1 to 20 wt.%.

The alkaline earth metal hydroxides are calcium and barium hydroxides. Among them, calcium hydroxide is particularly preferred.

Reaction conditions

In carrying out the present invention, calcium or barium hydroxide is used ordinarily in an amount of at least 1 mol, preferably at least 1.5 mol, per mol of the 2,3-dihalopropionic acid derivative or at least 0.8 mol, preferably at least 1 mol, per mol of the α-haloacrylic acid derivative. Although the maximum limit of the amount of calcium or barium hydroxide is not particularly provided, it is ordinarily up to about 50 mol, preferably up to about 10 mol, per mol of the substrate in view of the facility of the stirring and economy thus afforded.

The amount of ammonia is usually at least 1 mol, preferably at least 2 mol, per mol of the substrate. Although the maximum limit of the amount of ammonia is also not particularly provided, it is ordinarily up to about 100 mol, preferably up to about 50 mol, per mol of the substrate for consideration of the device and economy.

Any pertinent combination of the reaction temperature with the reaction time can be selected. For example, the reaction can be carried out at 0° to 200° C. for 10 min to 100 h, preferably at 50° to 150° C. for 30 min to 50 h.

RECOVERY OF THE SALTS

Azirdine-2-carboxylic acid salts

The aziridine-2-carboxylic acid salts which can be recovered according to the present invention are those shown by the following formula (BI):

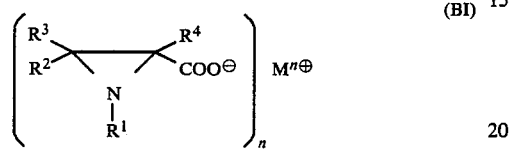

wherein:
$R^1$, $R^2$, $R^3$ and $R^4$ may be the same or different and represent each a hydrogen atom or a hydrocarbon residue having 1 to 10 carbon atoms;
M represents a cation selected from the group consisting of ammonium ion and metal ions; and n represents a valence of M.

Examples of $R^1$, $R^2$, $R^3$ and $R^4$ include hydrogen atom, and methyl, ethyl, propyl, butyl, amyl, hexyl, octyl, decyl, phenyl, tolyl, naphthyl and cyclohexyl groups. In a preferred combination thereof, $R^1$, $R^2$, and $R^4$ each represent a hydrogen atom, and $R^3$ represents a hydrogen atom, methyl group or phenyl group. It is particularly preferred that all of $R^1$, $R^2$, $R^3$ and $R^4$ represent a hydrogen atom.

Examples of the cations M include ammonium, lithium, sodium, potassium, beryllium, magnesium, calcium, strontium, barium, boron, aluminum, gallium, germanium, tin, titanium, zirconium, vanadium, iron, cobalt, nickel, copper, silver and zinc. Among them, ammonium, lithium, sodium, potassium, magnesium, calcium and barium are preferred, and more preferred are lithium, sodium, potassium, calcium and barium. Calcium and barium are the most preferred.

The aziridine-2-carboxylic acid salts to be treated according to the present invention contain at least inorganic salts as impurities. The term "containing at least inorganic salts as impurities" herein does not indicate that the aziridine-2-carboxylic acids contain only the inorganic salt impurities but it indicates that impurities other than said inorganic salt impurities can also be removed by the purification process of the present invention.

The inorganic salt impurities and other impurities comprise ordinarily inorganic salts by-produced unavoidably in the formation of the aziridine-2-carboxylic acid salt, reactants used in excessive amounts and oligomers of by-products formed by side reactions such as aziridine-2-carboxylic acid salts which are supposedly 1-(2-amino-2-carboxyethyl)aziridine-2-carboxylic acid salts. Further, the impurities may also be compounds added to an aqueous solution of a synthesized aziridine-2-carboxylic acid salt for the purpose of stabilizing the aziridine-2-carboxylic acid salt. Examples of the inorganic salts include ammonium salts such as ammonium chloride, ammonium bromide, ammonium iodide and ammonium sulfate; and halides and sulfates of alkali metals and alkaline earth metals such as lithium, sodium, potassium, magnesium and calcium. However, the inorganic salts are not limited to these examples. Examples of other impurities include alkali metal or alkaline earth metal hydroxides used in an excess amount in the formation of the aziridine-2-carboxylic acid salts and by-products formed by the side reactions.

Examples of preferred solutions of the aziridine-2-carboxylic acid salts containing the inorganic salts and other impurities include (1) an aqueous solution obtained by reacting an α-halo-β-aminopropionic acid derivative of the following formula (BII) or an α-amino-β-halopropionic acid derivative of the following formula (BIII) with an alkali metal or alkaline earth metal hydroxide and (2) an aqueous solution obtained by reacting an α,β-dihalopropionic acid derivative of the following formula (BIV) or an α-haloacrylic acid derivative of the following formula (BV) with ammonia in the presence of calcium hydroxide:

wherein:
X represents a halogen atom selected from the group consisting of chlorine, bromine and iodine;
Y represents a carboxyl group, carbamoyl group, alkoxycarbonyl group in which the alkoxy group has 1 to 8 carbon atoms, or cyano group;
Z represents a carbamoyl group, alkoxycarbonyl group in which the alkoxy group has 1 to 8 carbon atoms, or cyano group; and
$R^3$ represents a hydrogen atom or a hydrocarbon residue having 1 to 10 carbon atoms. Among these, an aqueous solution obtained by reacting an α,β-dihalopropionic acid derivative of the formula (BIV) or an α-haloacrylic acid derivative of the formula (BV) with ammonia in the presence of calcium hydroxide or barium hydroxide is particularly preferred.

PURIFICATION STEPS

Cation exchanger bed

The ion exchanger to be packed in a cation exchanger bed, which comprises the purification means of the present invention, is a special cation exchanger selected from the group consisting of strongly acidic cation exchangers of metal salt form, weakly acidic cation exchangers of metal salt form and weakly acidic cation exchangers of H form. Among these, the strongly acidic cation exchangers of metal salt form are particularly preferred. The term "strongly acidic cation exchangers" indicates that the cation exchange group contained therein is a sulfonic acid group. Therefore, the cation exchangers used in the present invention do not include those containing sulfonic acid group in its H-form, since the strongly acidic cation exchangers of H form have excessively high adsorption activity for the purification or recovery of the specified substances to be treated, i.e. the aziridine-2-carboxylic acid salts containing inorganic impurities. It will be understood that the H-form cation exchangers can be used for the purpose of the present invention after converting them substantially to cation exchangers of metal salt form with an aqueous solution of an aziridine-2-carboxylic acid salt containing inorganic salts.

In the cation exchangers of metal salt form, the metal ions may be selected suitably. Preferred examples of the metal ions include sodium, potassium, magnesium, zinc, cobalt, copper, manganese, nickel, calcium, lead, barium, chromium, aluminum and iron ions. Particularly preferred are sodium, potassium and calcium ions. Among these, calcium ion is the most preferred.

Examples of the ion exchange groups in the cation exchangers include sulfonic acid group, carboxyl group, phenol group, phosphoric acid group, phosphoric acid group and phosphinic acid group. Among these, the sulfonic acid group, carboxyl group and phosphoric acid group are preferred. The sulfonic acid group is particularly preferred.

The base to which the ion exchange group of the cation exchanger is bonded is not particularly limited. The bases include, for example, synthetic high polymers such as styrene resin, phenolic resin, acrylic or methacrylic resin, polyvinyl alcohol or its partially carbonized product, carbon fiber, polyacrylamide, polyphenylene ether, polysulfone, polyesters and fluorine resin; natural high polymers such as cellulose, agarose and dextran; and inorganic substances such as zeolite, silica, alumina, titania and hydroxyapatite. These bases are frequently modified by a chemical treatment such as crosslinking or surface treatment for the purpose of improving the mechanical strength, reducing the degree of swelling or shrinkage, improving the bonding property to the ion exchange group or preventing the coming-off of the ion exchange group.

Among the above-mentioned bases, preferred are the styrene resin, acrylic or methacrylic resin, partially carbonized product of polyvinyl alcohol, and cellulose. Among these, styrene resin is particularly preferred. The most preferred is a styrene resin comprising substantially a copolymer of divinylbenzene and styrene. The term "comprising substantially" indicates that the comonomers are mainly the divinylbenzene and styrene or that the styrene resin comprises mainly the copolymer.

The form of the cation exchanger is not particularly limited so long as it can be packed to form a bed. The cation exchanger may be in the form of, for example, beads, fibers, pulverized products or products obtained by shaping the pulverized products into granules, pellets, sheets or cloths by a suitable means. Among these, the beads, fibers and granules are preferred. Particularly, beads are preferred.

When the cation exchanger is in the form of beads or pulverized products, the average particle diameter thereof is ordinarily 5 to 2,000$\mu$, preferably 50 to 1,000$\mu$, more preferably 100 to 500$\mu$. The particle size distribution is preferably narrow. When the average particle diameter of beads is less than 5$\mu$, the pressure loss across the bed of the beads is large, and a high pressure device is necessitated, industrially unfavorably, although a high separation capacity is exhibited. When the average particle diameter exceeds 2,000$\mu$, the separation capacity is reduced seriously and unfavorably, though the pressure loss is small.

When the cation exchanger is fibrous, its average diameter is ordinarily 0.1 to 100$\mu$, preferably 1 to 70$\mu$ and particularly preferably 5 to 50$\mu$, and its average length is 50 to 2,000$\mu$, preferably 100 to 1,000$\mu$ and particularly preferably 200 to 800$\mu$. When the average diameter is less than 0.1$\mu$ and/or the average fiber length is less than 50$\mu$, the pressure loss is unfavorably large although the separation capacity is high. When the average diameter exceeds 100$\mu$ and/or the average fiber length exceeds 2,000$\mu$, the separation capacity is low and the packing density is also unfavorably low.

When the cation exchanger is in the form of granules or pellets, the average diameter thereof is ordinarily 200 to 8,000$\mu$, preferably 500 to 5,000$\mu$ and particularly preferably 1,000 to 3,000$\mu$.

When the cation exchanger is in the form of a sheet or cloth, it may be cut into strips of about 1 to 5 mm width to facilitate the packing thereof.

Particularly preferred examples of the abovementioned cation exchangers are strongly acidic styrene-based cation exchange resins of sodium, potassium or calcium form having a degree of cross linking (divinylbenzene content) of 1 to 20%, in the form of beads of average particle diameter of 100 to 500$\mu$, sulfonic acid group as the ion exchange group and an exchange capacity of 0.5 to 5 meq/ml. Examples of the preferred cation exchangers include fibrous, strongly acidic cation exchangers of sodium, potassium or calcium form having a longer diameter of 10 to 50$\mu$, shorter diameter of 5 to 20$\mu$, length of 200 to 800$\mu$ and exchange capacity of 0.5 to 5 meq/g (dry basis) obtained by sulfonating a dehydrated partially carbonized polyvinyl alcohol fibers.

The combination of the cation exchanger, aziridine-2-carboxylic acid salt and inorganic salt impurity is not limited. However, a combination in which a cation which is common to the compounds concerned is included is preferred. Particularly, a combination in which all the cations are calcium ion is preferred.

Purification

In the process of the present invention, the aziridine-2-carboxylic acid salt is recovered by feeding an aqueous solution thereof into a front end of bed comprising the above-mentioned cation exchanger, then feeding water thereinto and recovering a fraction of the aziridine-2-carboxylic acid salt eluted at a rear end of the bed, this fraction being completely or incompletely free from the other components.

Prior to the feeding of the aqueous solution of the aziridine-2-carboxylic acid salt, the bed is ordinarily filled with water. Further, before the aqueous solution of the aziridine-2-carboxylic acid is contacted with the cation exchanger, this aqueous solution is ordinarily kept from mixing with water to be fed subsequently. For this purpose, water is taken out through the rear end of the packed bed in an amount corresponding to the amount of the aqueous solution of the aziridine-2-carboxylic acid salt to be fed prior to the feeding or water, and/or the diameters of inlet tubes for the aqueous aziridine-2-carboxylic acid salt solution and water are made sufficiently smaller than that of the packed bed so as to realize a piston flow.

The water used for the elution is not necessarily a buffer solution. Ordinary water such as tap water, industrial water, ion-exchanged water or distilled water can be used depending on the use of the aziridine-2-carboxylic acid salt to be obtained. When buffer water is used, the recovered aziridine-2-carboxylic acid salt must be further purified to remove the buffering component.

The temperature of the aqueous aziridine-2-carboxylic acid salt solution and water used as the eluent is ordinarily 0° to 70° C., preferably 5° to 50° C. and more preferably 10° to 30° C. When the temperature exceeds 70° C., the aziridine-2-carboxylic acid salt is denatured unfavorably. At a temperature below 0° C., water is crystallized unfavorably.

The concentration of the aziridine-2-carboxylic acid salt in its aqueous solution to be purified is not particularly limited. Ordinarily, it is 0.01 to 80%, preferably 0.1 to 50% and more preferably 1 to 30%. The term "aqueous solution of aziridine-2-carboxylic acid salt" herein includes a solution containing a water-soluble organic solvent such as an alcohol dissolved therein.

The amount of the aqueous solution of the aziridine-2-carboxylic acid salt to be fed into the packed bed is ordinarily 0.01 to 150%, preferably 0.1 to 100%, more preferably 1 to 50%, based on the volume of the bed of the ion exchanger. When the amount is less than 0.01%, the recovering efficiency of the aziridine-2-carboxylic acid salt is low, and, on the contrary, when it exceeds 150%, the capacity of separating the aziridine-2-carboxylic acid salt from the other components is reduced unfavorably.

The feeding rates of the aqueous solution of the aziridine-2-carboxylic acid salt and water vary depending on the variety of the cation exchanger to be packed in the bed. The liquid space velocity is ordinarily 0.01 to 100 $h^{-1}$, preferably 0.1 to 50 $h^{-1}$. When it is less than 0.01 $h^{-1}$, the recovering efficiency of the aziridine-2-carboxylic acid salt is low, and, on the contrary, when it exceeds 100 $h^{-1}$, the separation capability is lowered unfavorably.

The diameter of the bed is not particularly limited and is determined according to the amount of the aziridine-2-carboxylic acid salt to be recovered.

The length of the packed bed varies depending on the separating capability of the cation exchanger to be packed therein. The length is ordinarily about 5 cm to 10 m, preferably about 10 cm to 5 m.

Although the bed used in the process of the present invention may be either vertical or horizontal, the vertical one is ordinarily preferred. In the process of the present invention, the aziridine-2-carboxylic acid salt is recovered by separating the same from the inorganic salt impurity, taking advantage of the difference between the affinity of a specified cation exchanger charged in a fixed bed for the impurity and the affinity of the exchanger for the aziridine-2-carboxylic acid salt according to liquid chromatography. Any of known liquid chromatographic separation system suchs as a batch system, moving bed system or pseudo moving bed system can be employed.

Even when the separation of the aziridine-2-carboxylic acid salt from the other components is insufficient, the separation can be made complete by increasing the length of the packed bed or by employing a multiple stage-system in which a fraction containing two or more components is recycled at least once into the front end of the packed bed. When water used as the eluent is introduced therein, the inorganic salt impurity is eluted out first and then the aziridine-2-carboxylic acid salt is eluted out. The fraction of the intended aziridine-2-carboxylic acid salt is taken to recover the purified aziridine-2-carboxylic acid salt. When an alkali metal or alkaline earth metal hydroxide is contained as another impurity, it is eluted out simultaneously with the inorganic salt. When α-chloropropionic acid is contained therein, it is eluted out after the inorganic salt but prior to the aziridine-2-carboxylic acid salt. When an oligomer of the aziridine-2-carboxylic acid salt is contained therein, it is eluted after the aziridine-2-carboxylic acid salt.

When the separation is carried out continuously by introducing the aqueous solution of the aziridine-2-carboxylic acid salt and the eluent (water) alternately, the aziridine-2-carboxylic acid salt can be recovered efficiently by employing the above-mentioned multiple stage recycle process.

Figure 3:
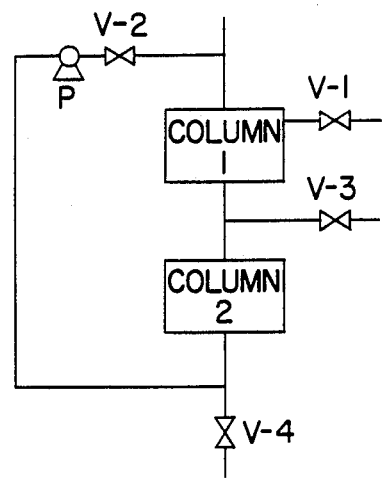
FIG. 3 is a diagram showing a two-column type separation device.

An example of the process will now be described with reference to FIG. 3 which shows schematically a device used in the present invention.

The first stage: An aqueous solution of an aziridine-2-carboxylic acid salt containing an inorganic salt as an impurity is fed into the upper end of a column 1 through a valve 1, and then water is fed thereinto to elute a major part of the inorganic impurity through a valve 4 while a valve 2 and a valve 3 are kept closed.

The second stage: The valves 1 and 4 are closed, and the valve 2 is opened to release a fraction comprising a boundary between the inorganic salt layer and the aziridine-2-carboxylic acid salt layer through the bottom of a column 2 and recycled into the upper end of the column 1 by means of a circulation pump.

The third stage: The valve 2 is closed and the valves 3 and 4 are opened. Water is fed through the valve 3, and a major part of the aziridine-2-carboxylic acid salt eluted through the valve 4 is recovered.

The fourth stage: The valves 3 and 4 are closed, and the valve 2 is opened. An end fraction of the eluted aziridine-2-carboxylic acid salt is recycled from the bottom of the column 2 into the upper end of the column 1 by means of the circulation pump.

The above described first to the fourth stages are repeated. A substantially stationary state is realized after 10 to 15 times repetition when the conditions are selected suitably.

Ordinarily, the amount of the fraction to be recycled in the second and the fourth stages is about 1/10 to 1/5 of the total volume of the column. The column 2 is about two times as long as the column 1.

The performance of the cation exchanger is reduced occasionally after it is used repeatedly over a long period of time according to the process of the present invention. When the cation exchanger is of the metal salt type, the performance can be increased again by a process wherein the exchanger is treated with a mineral acid after taking the same out of the packed bed or while it is kept in the bed and then treated with a metal ion-containing aqueous solution, or, alternatively, by a process wherein the exchanger is treated with a metal ion-containing aqueous solution (for example, an aqueous solution of calcium hydroxide or calcium chloride when the cation exchanger to be treated is of calcium salt type) without the treatment with the mineral acid. When the cation exchanger is a weakly acidic one of H-type, the performance can be increased again by treating the same with a mineral acid. After the performance of the cation exchanger has been recovered by the above-mentioned process, it is washed with water and then used again.

EXPERIMENTAL EXAMPLES

In the following experiments, the starting materials and the products were analyzed according to high-performance liquid chromatography.

Example A1

2.5 g (15.9 mmol) of methyl 2,3-dichloropropionate, 22 g of 12.5% aqueous ammonia (161.8 mmol of ammonia) and 3.6 g (48.6 mmol) of calcium hydroxide were charged into a 100-ml autoclave, and the reaction was carried out at 90° C. for 5 hours (h.).

The reaction mixture was filtered and the filtrate was analyzed to reveal that the yield of calcium aziridine-2-carboxylate was 95.3%.

Examples A2 to A19

The procedure of Example 1 was repeated except that methyl 2,3-dichloropropionate was replaced with 15.9 mmol of another starting material.

The results are shown in Table 1.

TABLE 1

| Example | Starting material | Yield of calcium-aziridine-2-carboxylate (%) |
|---|---|---|
| A2 | ethyl 2,3-dichloropropionate | 95.0 |
| A3 | n-butyl 2,3-dichloropropionate | 89.7 |
| A4 | n-octyl 2,3-dichloropropionate | 80.8 |
| A5 | benzyl 2,3-dichloropropionate | 91.3 |
| A6 | 2,3-dichloropropionic acid amide | 94.8 |
| A7 | 2,3-dichloropropionic acid N-methylamide | 87.6 |
| A8 | 2,3-dichloropropionic acid N,N-dimethylamide | 83.4 |
| A9 | 2,3-dichloropropionitrile | 95.1 |
| A10 | methyl α-chloroacrylate | 95.6 |
| A11 | n-propyl α-chloroacrylate | 91.7 |
| A12 | α-chloroacrylamide | 94.8 |
| A13 | α-chloro-N-methyacrylamide | 88.3 |
| A14 | α-chloroacrylonitrile | 95.3 |
| A15 | methyl 2,3-dibromoprionate | 95.8 |
| A16 | 2,3-dibromopropionic acid amide | 94.9 |
| A17 | 2,3-dibromopropionitrile | 95.4 |
| A18 | methyl α-bromoacrylate | 94.7 |
| A19 | α-bromoacrylonitrile | 94.9 |

Example A20

The procedure in Example A1 was repeated except that aqueous ammonia was replaced with a mixture of 22 g of 12.5% aqueous ammonia and 20 g of methanol. The yield of calcium aziridine-2-carboxylate was 88.5%.

Example A21

92 g (667 mmole as $NH_3$) of aqueous ammonia and 22.5 g (67.6 mmole) of barium hydroxide octahydrate, $Ba(OH)_2 \cdot 8H_2O$, were added to a 200 ml-flask equipped with a reflux condenser, and 4.28 g (33.8 mmole) of 2,3-dichloropropionitrile was added thereto, and the mixture was subjected to reaction at 80° C. for 2 h.

The yield of barium aziridine-2-carboxylate obtained was 83.2%.

Comparative Example A1

The procedure in Example A1 was repeated except that calcium hydroxide was replaced with 97.2 mmol of sodium hydroxide. The yield of sodium aziridine-2-carboxylate was as low as 42.3%.

Comparative Example A2

The procedure in Example A14 was repeated except that calcium hydroxide was replaced with 97.2 mmol of sodium hydroxide. The yield of sodium aziridine-2-carboxylate was as low as 38.7%.

Referential Example B1

9.1 g of 2,3-dichloropropionitrile was added to a slurry comprising 100 g of 12.5% aqueous ammonia and 10.9 g of calcium hydroxide, which slurry was kept at 55° C. The mixture was stirred at 55° C. for 1 h, and then the reaction was carried out at 70° C. for an additional 5 h. Ammonia was removed by means of a rotary evaporator, and then calcium hydroxide was filtered out to obtain 85.0 g of an aqueous solution comprising 8.81% of calcium aziridine-2-carboxylate, 9.60% of calcium chloride, 0.10% of calcium hydroxide and by-products. The yield of calcium aziridine-2-carboxylate determined by high-performance liquid chromatography (the same shall apply hereinafter) was 96.0%.

Referential Example B2

98.5 g of 18.8% aqueous solution of β-chloroalanine was added dropwise to 86.0 g of 18.6% aqueous sodium hydroxide solution kept at 50° C. over 30 min, and then the reaction was carried out at 50° C. for an additional 10 h to obtain 184.5 g of an aqueous solution containing 8.1% of sodium aziridine-2-carboxylate, 4.8% of common salt, 2.2% of sodium hydroxide and by-products. The yield of sodium aziridine-2-carboxylate was 91.0%.

Referential Example B3

The procedure in Referential Example B1 was repeated except that 2,3-dichloropropionitrile was replaced with 12.6 g of methyl 2,3-dichlorobutyrate to obtain 67.0 g of an aqueous solution containing 10.7% of calcium 3-methylaziridine-2-carboxylate, 12.2% of calcium chloride, 0.10% of calcium hydroxide and by-products. The yield of calcium 3-methylaziridine-2-carboxylate was 81.0%.

Example B1

A beads-like, strongly acidic styrene/divinylbenzene cation exchange resin of Na+ form ("Diaion SK1BS"; a product of Nippon Rensui Co., Japan) having an average particle diameter of 180μ, degree of crosslinking of 8% and exchange capacity of 2.1 meq/ml was ion-exchanged into $Ca^{2+}$ form and was then charged into a column having an inner diameter of 1.0 cm and a height of 40 cm. The column was filled up to the brim with distilled water. 3.0 ml of the aqueous solution obtained in Referential Example 1 was charged into the column, and water was taken out through the bottom of the column until the liquid surface was lowered to the same level as the resin surface. Then, distilled water was introduced thereinto through the top of the column at a liquid hourly space velocity (LHSV) of 1 $h^{-1}$ at 20° C. The bottom of the column was connected to a differential refractometer, and the eluted components were monitored continuously with a recorder.

Figure 2:
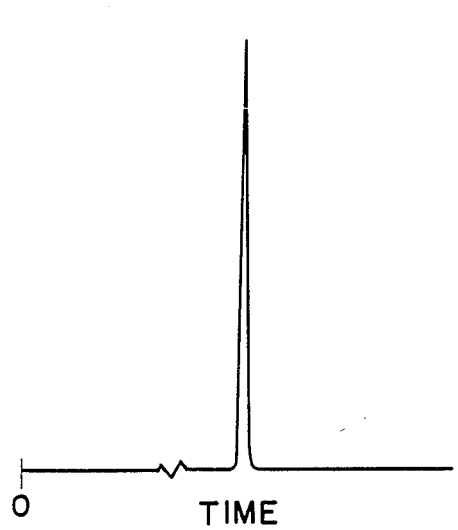
FIG. 2 is a chromatogram obtained when a calcium aziridine-2-carboxylate fraction shown in FIG. 1 was taken out and analyzed according to high-performance liquid chromatography.

An elution curve thus obtained is shown in FIG. 1. Calcium hydroxide and calcium chloride were eluted first through the bottom of the column, and then calcium aziridine-2-carboxylate was eluted. The fraction of calcium aziridine-2-carboxylate was taken. The recovery was 98.5%. This fraction was analyzed according to the high performance liquid chromatography to reveal that impurities were substantially not contained therein (see FIG. 2).

Example B2

The procedure in Example B1 was repeated except that the aqueous, calcium aziridine-2-carboxylate-forming reaction solution was replaced with the aqueous, calcium 3-methylaziridine-2-carboxylate-forming reaction solution obtained in Referential Example 3. The recovery of calcium 3-methylaziridine-2-carboxylate was 92.1%.

Example B3

The procedure in Example B1 was repeated except that the aqueous, calcium aziridine-2-carboxylate-forming reaction solution was replaced with the aqueous, sodium aziridine-2-carboxylate-forming reaction solution and that the cation exchange resin of $Ca^{2+}$ form was replaced with a beads-like, strongly acidic styrene/divinylbenzene cation exchange resin of $Na+$ form (trade name: Diaion SK 104S; a product of Nippon Rensui Co.) (not ion-exchanged) having an average particle diameter of 260μ, degree of crosslinking of 4% and exchange capacity of 1.4 meq/ml. The recovery of sodium aziridine-2-carboxylate was 98.9%.

Example B4

The procedure in Example B1 was repeated except that the beads-like, strongly acidic cation exchange resin of $Ca^{2+}$ form was replaced with an ion exchange fiber obtained by ion-exchanging a fibrous, strongly acidic cation exchanger (trade name: NIchivi Ion Exchange Fiber; a product of Nichivi Co.) having a longer diameter of 30μ, shorter diameter of 10μ, length of 500μ and total ion exchange capacity of 3.1 meq/g (dry basis) obtained by partially carbonizing polyvinyl alcohol fibers and sulfonating the same which was then ion-exchanged into a $Ca^{2+}$ form and that LHSV was altered to 10 $h^{-1}$. The recovery of calcium aziridine-2-carboxylate was 85.1%.

Comparative Example B1

The procedure in Example B1 was repeated except that the temperature of distilled water was altered to 80° C. The recovery of calcium aziridine-2-carboxylate was as low as only 66.7%, and the calcium aziridine-2-carboxylate fraction taken out contained various impurities and had a low purity.

Comparative Example B2

50 g of the aqueous, calcium aziridine-2-carboxylate solution obtained from the reaction shown in Referential Example B1 was concentrated to 20 g by means of a rotary evaporator. A small amount of calcium hydroxide thus precipitated was filtered out. The filtrate was heated to 60° C. 70 ml of ethanol was added thereto, and the mixture was left to stand in a refrigerator at 5° C. overnight. A solid thus precipitated out was recovered by filtration, washed with ether and dried in vacuum. The yield was 0.911 g. The solid was analyzed to reveal that it comprised 58.5% of calcium aziridine-2-carboxylate and 39.2% of calcium chloride. That is, the recovery and purity of calcium aziridine-2-carboxylate were as low as only 12.1% and 58.5%, respectively.

Example B5

The procedure in Example B1 was repeated except that the beads-like, strongly acidic cation exchange resin of $Ca^{2+}$ form was replaced with a beads-like, weakly acidic acrylic acid/divinylbenzene cation exchange resin of H-form (trade name: Diaion WK 20; a product of Nippon Rensui Co.) having an average particle diameter of 400μ and exchange capacity of 3.5 meq/ml and that the amount of the aqueous, calcium aziridine-2-carboxylate solution obtained in Referential Example 1 was altered from 3 ml to 1 ml. The recovery of calcium aziridine-2-carboxylate was 93.0%.

Example B6

The procedure in Example B1 was repeated except that the strongly acidic cation exchange resin of $Ca^{2+}$ form was replaced with a beads-like, strongly acidic cation exchange resin of H-form (trade name: Diaion SK1BS; a product of Nippon Rensui Co.). Even ten hours after the initiation of the introduction of distilled water, calcium aziridine-2-carboxylate was not eluted out.

The aqueous solution obtained in Referential Example B1 was introduced therein at 20° C. at a space velocity of 0.5 for 5 h and then the resin was washed by introducing distilled water therein at 20° C. at SV of 2 for 3 h. Thereafter, the aqueous solution obtained in Referential Example B1 and distilled water were introduced therein in the same manner as in Example B1. The recovery of calcium aziridine-2-carboxylate was 98.3%.

What is claimed is:

1. A process for recovering aziridine-2-carboxylic acid salts, which comprises:
    (a) feeding an aqueous solution of an aziridine-2-carboxylic acid salt selected from the group consisting of a calcium salt and a barium salt containing at least an inorganic salt which is ionizable in said aqueous solution as an impurity into a front end of a bed of a cation exchanger selected from the group consisting of a strongly acidic cationic exchanger of a metal salt form wherein the metal is selected from the group consisting of calcium and barium, a weakly acidic cation exchanger of a metal salt form where the metal is selected from the group consisting of calcium and barium and a weakly acidic cation exchanger of H-form, and then
    (b) feeding water thereinto and recovering a fraction of the aziridine-2-carboxylic acid salt salt eluted at a rear end of the bed.

2. The process according to claim 1, wherein the aziridine-2-carboxylic acid salts have the formula (BI):

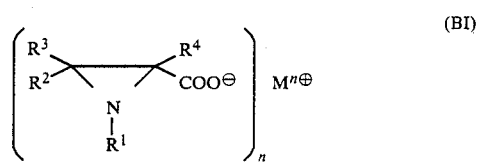

wherein $R^1$, $R^2$, $R^3$ and $R^4$ are the same or different and each represent a hydrogen atom or a hydrocarbon group having 1 to 10 carbon atoms; M represents a cation selected from the group consisting of a calcium ion and a barium ion; and n re presents a valence of M.

3. The process according to claim 2, wherein $R^1$, $R^2$, $R^3$ and $R^4$ each represent a hydrogen atom.

4. The process according to claim 2, wherein M is ammonium, lithium, sodium, potassium, calcium and barium.

5. The process according to claim 4, wherein M is calcium or barium.

6. The process according to claim 1, wherein the aqueous solution of an aziridine-2-carboxylic acid salt containing at least an inorganic salt as an impurity is one obtained by reacting an α-halo-β-aminopropionic acid compound of the formula (BII) or an α-amino-β-halopropionic acid compound of the formula (BIII) with calcium hydroxide or barium hydroxide or one obtained by reacting an α, β-dihalopropionic acid compound of the formula (BIV) or an α-haloacrylic acid compound of the formula (BV) with ammonia in the presence of calcium hydroxide or barium hydroxide:

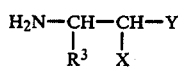 (BII)

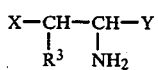 (BIII)

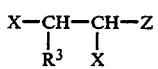 (BIV)

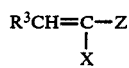 (BV)

wherein X represents a halogen atom selected from the group consisting of chlorine, bromine and iodine; Y represents a carboxyl group, carbamoyl group, alkoxycarbonyl group in which the alkoxy group has 1 to 8 carbon atoms or a cyano group; Z represents a carbamoyl group, alkoxycarbonyl group in which the alkoxy group has 1 to 8 carbon atoms or a cyano group; and $R^3$ represents a hydrogen atom or a hydrocarbon group having 1 to 10 carbon atoms.

7. The process according to claim 6, wherein $R^1$, $R^2$, $R^3$ and $R^4$ each represent a hydrogen atom.

8. The process according to claim 1, wherein the cation exchanger is a bead-shaped, strongly acidic cation exchange resin of a sodium, potassium or calcium form comprising a styrene resin comprising a copolymer of divinylbenzene and styrene as the base and having a divinylbenzene content of 1 to 20%, an average particle diameter of 100 to 500μ, a sulfonic acid group as the ion exchange group and an exchange capacity of 0.5 to 5 meq/ml.

9. The process according to claim 1, wherrein the temperature of the liquid to be introduced into the bed comprising the cation exchanger is 5° to 50° C.

10. The process according to claim 6, wherein X is chlorine.

11. The process according to claim 1, wherein said water eluant is at a temperature of about 0° to 70° C.

12. The process according to claim 1, wherein said aqueous solution of the aziridine-2-carboxylic acid salt has a concentration of about 0.01 to 80%.

13. The process according to claim 1, wherein said aqueous solution of the aziridine-2-carboxylic acid is fed into the cation exchanger bed in the amount of 0.01 to 150% of the volume of the ion exchange bed.

14. The process according to claim 1, wherein the aqueous solution of the aziridine-2-carboxylic acid is fed into the cation exchanger with a liquid space velocity of 0.01 to 100 $h^{-1}$.

15. The process according to claim 1, wherein the cation exchanger bed has a length of about 5 cm to 10 m.

* * * * *